United States Patent
Babichenko et al.

(10) Patent No.: US 7,843,556 B2
(45) Date of Patent: Nov. 30, 2010

(54) PORTABLE DEVICE AND METHOD FOR ON-SITE DETECTION AND QUANTIFICATION OF DRUGS

(75) Inventors: Sergey Babichenko, Tallinn (EE); Enn Erme, Tartu (EE); Tatjana Ivkina, Apex, NC (US); Larisa Poryvkina, Tallinn (EE); Vitaly Sominsky, Apex, NC (US)

(73) Assignee: NarTest AS, Tallinn (EE)

( * ) Notice: Subject to any disclaimer, the term of this patent is extended or adjusted under 35 U.S.C. 154(b) by 618 days.

(21) Appl. No.: 11/579,427

(22) PCT Filed: May 13, 2004

(86) PCT No.: PCT/CA2004/000710

§ 371 (c)(1),
(2), (4) Date: Jan. 22, 2008

(87) PCT Pub. No.: WO2005/111586

PCT Pub. Date: Nov. 24, 2005

(65) Prior Publication Data

US 2008/0192249 A1    Aug. 14, 2008

(51) Int. Cl.
*G01N 21/00* (2006.01)
(52) U.S. Cl. ..................................... 356/73

(58) Field of Classification Search ............. 356/72–73, 356/301
See application file for complete search history.

(56) References Cited

U.S. PATENT DOCUMENTS

| | | | |
|---|---|---|---|
| 3,814,939 A | 6/1974 | Parker et al. | |
| 4,241,998 A | 12/1980 | Farkas et al. | |
| 4,330,207 A | 5/1982 | Nogami et al. | |
| 4,681,444 A | 7/1987 | Ferber et al. | |
| 5,500,536 A | 3/1996 | Nogami et al. | |
| 5,742,380 A * | 4/1998 | Ronn | 356/39 |
| 5,801,828 A | 9/1998 | Collins | |
| 5,843,790 A | 12/1998 | Ronn | |
| 6,124,937 A | 9/2000 | Mittenzwey et al. | |

FOREIGN PATENT DOCUMENTS

EP    0 481 823    4/1995

* cited by examiner

*Primary Examiner*—Tarifur Chowdhury
*Assistant Examiner*—Abdullahi Nur
(74) *Attorney, Agent, or Firm*—Husch Blackwell Welsh Katz

(57) ABSTRACT

The present invention discloses a portable, reliable, automated and simple device using Spectral Fluorescence Signature technology (SFS) for fast and accurate drug detection, quantification and data storage. The present also discloses a method for using Spectral Fluorescence Signature technology (SFS) for fast and accurate drug detection, quantification and data storage. Such device and method needing not highly skilled personnel or specific background to run the tests.

33 Claims, 7 Drawing Sheets

A - A
M2:1

B - B

PORTABLE DEVICE AND METHOD FOR ON-SITE DETECTION AND QUANTIFICATION OF DRUGS

FIELD OF THE INVENTION

This invention relates the use of Spectral Fluorescence Signature technology (SFS) for on-site drug detection and quantification.

BACKGROUND OF THE INVENTION

Testing and quantifying street samples, for example for narcotics, with the current devices and methods known in the art, although some times very precise, still takes a long time and requires personnel with specific scientific backgrounds. Accordingly, legal actions and court proceedings depending on those analysis are frequently dismissed. Detection and quantification of street samples, including powder or solid form, or as crushed dried plants, or as tobacco from cigarettes (cigars), or in a liquid form is a complex task due to multi component samples constituting drug mixtures with adulterants and diluents in different ratios. Many devices known in the prior art for drug detection and quantification are bench top laboratory equipments. These are sophisticated equipments that, although precise, are costly and require a sample preparation step, a long time for issue of a result and require highly trained personnel to run the tests.

Some devices for drug detection, which are portable devices, are intended for detecting trace drug samples, which is not the purpose of this invention. These devices are limited to detecting specific (single) drug traces, mainly because these equipments cannot identify mixtures of unknown composition.

Three technologies are used at present for the task of street drug detection: Raman spectroscopy, infra red spectroscopy and fluorescence.

Although Raman spectroscopy is suitable for field operation, the selectivity in mixtures is doubtful and the data interpretation is questionable. Three major shortcomings limit the use of Raman spectroscopy for qualitative and quantitative analysis. Fluorescence is the major problem as even low levels of fluorescence can mask the Raman signal. The second problem arises due to absorbance effects of different components in such samples. The third problem is that because complex samples are studied in bulk, it is challenging to determine the identity of each compound when multiple peaks from several compounds are present in the same spectral region. Therefore the use of Raman spectroscopy in the investigation of colored samples or highly fluorescing and multi component sample is difficult. False results are frequent consequences of this situation.

The use of infrared spectroscopy is doubtful because the known device based on this technology is proposed for identification of drugs and other chemicals in clandestine labs, meaning that samples are not the real complex street samples with adulterants and diluents. Several shortcomings are known in this technology, such as that low energy flow of light sources in the infrared spectral range causes low sensitivity and low selectivity of this technique. Also, the numerous absorptions bands of solvent and water vapor in the air influence the interpretation of results. Furthermore, adulterants and diluents make the analysis of street drugs practically impossible without a complex preparation of the samples.

Fluorescence is a well known technology for the detection of organic substances and mixtures in various matrixes. However, presently there is no device or method aimed for the analysis of street drugs based on this technology, due to the specific spectral characteristics of street drugs as seen below:

complex and multi component character of the samples hampers analysis by conventional fluorescence techniques without preliminary separation of the components;

spectra overlapping and non-additive combination of fluorescence intensities caused by possible mutual interaction of the components;

variability of the fluorescent characteristics of the mixed sample caused by possible adulterants and diluents, and necessity to detect, or detect and quantify, simultaneously several components in a mixed sample.

Patents of the prior art for drug detection use different methodologies. For example, U.S. Pat. No. 5,648,047 to Kardish et al. and U.S. Pat. No. 4,840,912 to Glattstein disclose the use of color tests. U.S. Pat. No. 4,812,413 to Glattstein et al., U.S. Pat. No. 4,196,167 to Olsen and U.S. Pat. No. 6,194,898 to Magnuson et al., all use different kinds of methods, devices or kits.

In view of the foregoing, for a better and faster response to investigations and law enforcement actions, it is desirable that street samples to be diagnosed for the presence of narcotics and other components (if necessary) on-site by police officers, customs officers and others, using a simple and quick procedure without any requirement for special education or long training. There is also a demand for a method of, and a portable device for, detection of drugs in street samples where manual operations have to be minimized, simplified and able to be repeated. Further more, the proper preparation of the samples for correct measurements has to be done automatically, the detection accuracy has to be in accordance with the acting cut off levels as false positive and false negative results may result in inappropriately charging a person or with the possibility of missing a crime. Finally, analysis data have to be documented, safely stored and possibly transferred to a different site.

SUMMARY OF THE INVENTION

The present invention seeks to provide a device and a method of outstanding optical differentiation, recognition, detection and quantification together with a data storage capacity concerning one or several substances in a complex mixtures without preliminary separation and chemicals.

The present invention seeks to provide a portable, reliable, automated and simple device using Spectral Fluorescence Signature technology (SFS) for fast and accurate drug detection, quantification and data storage. The present invention also seeks to provide a method using Spectral Fluorescence Signature technology (SFS) for fast and accurate drug detection, quantification and data storage. Such device and method needing not highly skilled personnel or personnel with a specific scientific background to run the tests. Ideally, the method and device of this invention require no more skill and training than to required by a police officer using a breathalyzer. In one aspect of the invention, the present invention seeks to provide a portable device for detection and quantification of drugs in street samples including:

-CLAIM 1 will be inserted here before filing-

For purposes of discussion, street samples in this application are the forms of illegal traffic and sell of drugs of abuse. They are usually presented by mixture of drugs of abuse with adulterants and diluents at different ratio. Sometimes they may contain only adulterants and diluents without drugs of abuse. Among adulterants of street samples may be toxic substances in high concentrations.

DETAILED DESCRIPTION OF THE INVENTION

Figure 9A:
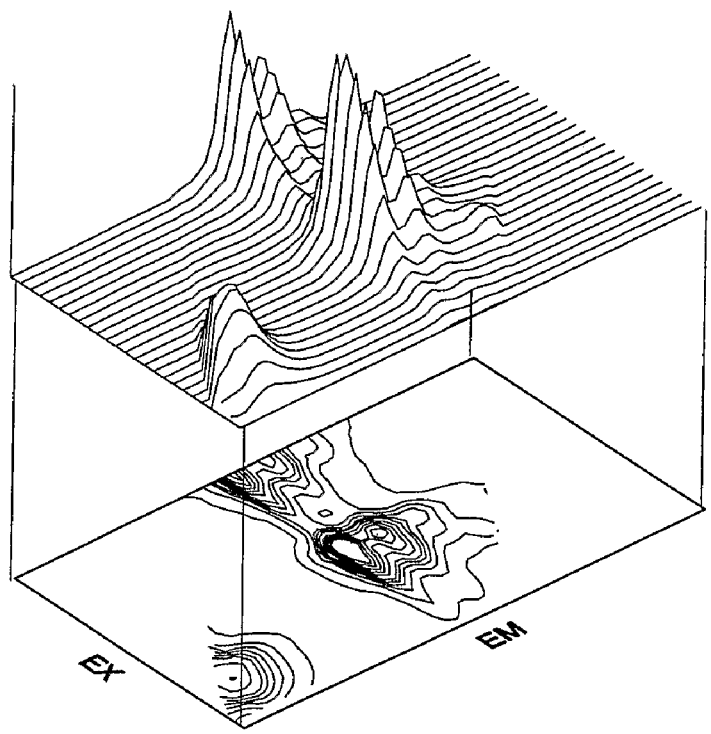
FIG. 9a is a diagrammatic representation of a Spectral Fluorescent Signature.
Figure 9B:
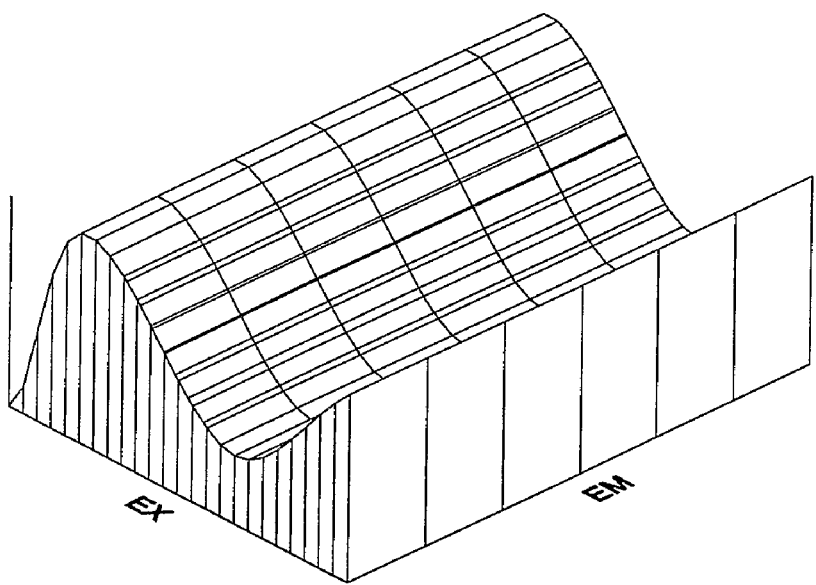
FIG. 9b is a diagrammatic representation of the absorption matrix.

The technology of Spectral Fluorescence Signatures (SFS) is effectively applied for detection and identification of organic impurities in a water matrix. This technique offers a 3-dimensional fluorescent pattern display of the sample. The three dimensions are: excitation wavelengths, emission wavelengths, and fluorescent intensity. These patterns can also be presented in a 2-dimensional spectral image of equal fluorescence intensity levels. FIG. 9a is showing a diagrammatic representation of a Spectral Fluorescent Signature presented in a 2-dimensional spectral image where EM is emission wavelengths and EX is excitation wavelengths, showing the different fluorescent intensity levels. FIG. 9b is a diagrammatic representation of the absorption matrix, which represents the values of optical absorption in the sample for every element of the SFS matrix. Different substances are revealed in different positions in the matrixes.

It is important to note that the level of fluorescent intensity is directly proportional to the amount, or concentration, of the compounds present in the mixture.

Since every chemical substance that has feature to emit the fluorescence has its own characteristic excitation and emission wavelengths, different substances generate different SFSs. The SFSs of the sought substances are previously measured and stored in the library for later reference. The fluorescent patterns of the untreated street sample being measured can then be compared to the SFS of these known library substances.

Figure 10:
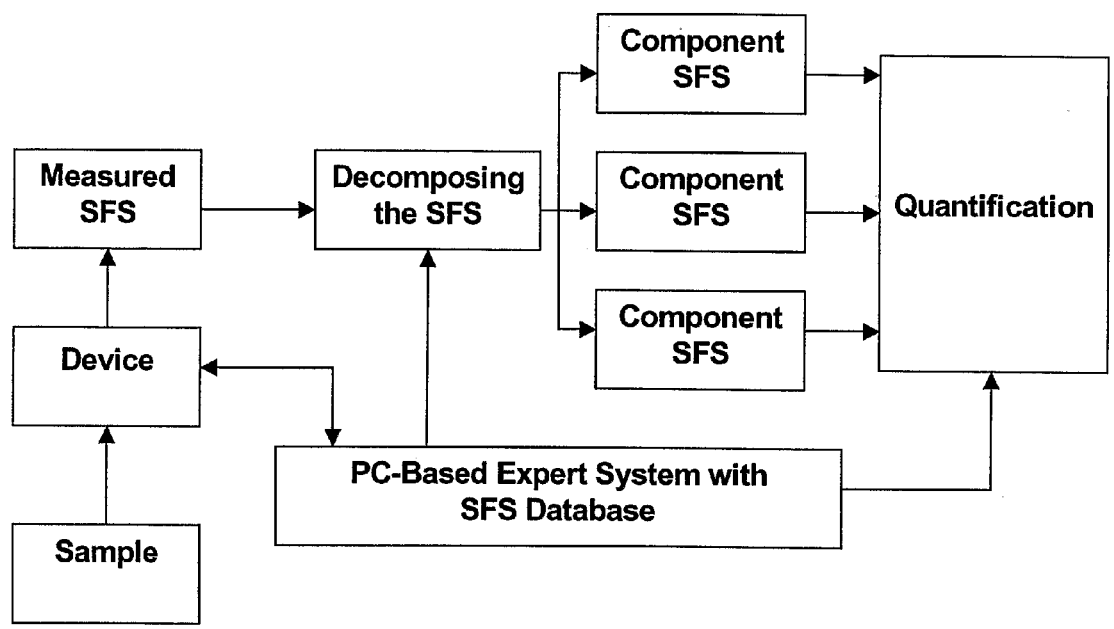
FIG. 10 is a diagrammatic representations of the recognition and quantification method.

In this way, different substances in a mixture can be recognised and quantified without requiring any reagents for sample preparation (or with a minimal preparation procedure). Another advantage of this library is that the background fluorescence as SFS is also measured. If the background fluorescence is fluctuating, it is taken into account by the expert system, thereby providing a more consistent and reliable result, as can be seen in FIG. 10 where a diagrammatic representations of the recognition and quantification method is shown.

The optical density of liquid samples that is controlled by photometric measurements is important feature of sample and is taken in account for calibration of fluorescence intensity versus concentration of the substances.

The following modifications on the SFS technique allow its use for the detection of drugs in street samples:

an additional spectral channel is used to measure absorption spectra in the analyzed sample—to take into account the influence of the non-fluorescing or highly absorbing components;

the absorption value is measured simultaneously with the fluorescence intensities at every step of excitation wavelength—to take into account possible photochemical processes;

the excitation, emission and absorption spectral windows and resolution are selected and fixed in a way to cover specific excitation/emission fluorescence and absorption bands of all major drugs, adulterants and diluents—it provides reliable screening of unknown composition in a sample for drug detection;

the measured SFS is accompanied with an absorption matrix (AM), and SFS & AM are treated as a united result of the measurement—AM adds one more dimension to 3-dimensional SFS in the information matrix, and therefore provides components recognition, when interaction between components takes place, and the united result (SFS & AM) are processed by computer system based on combination of preliminary prepared spectral library and specialized software consisting of identification, interaction verification and automatic calibration modules.

Figure 1:
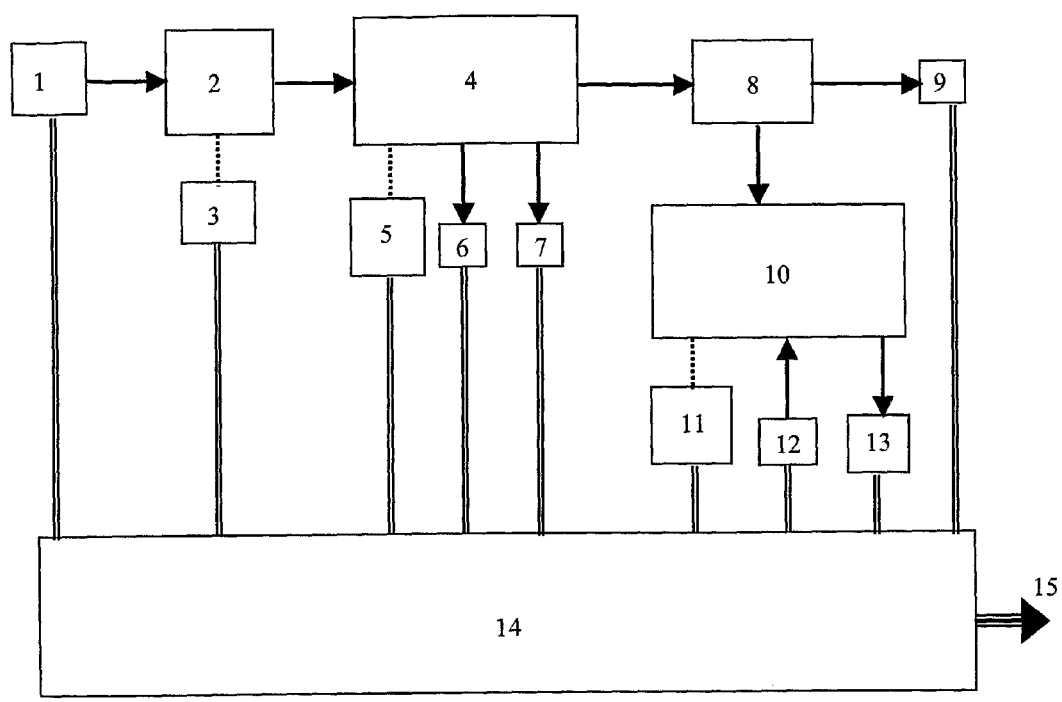
FIG. 1 is a block diagram of the device of the present invention.

The device of this invention, as shown in FIG. 1, includes optically connected an ultraviolet-visible (UV-VIS) light source 1, a condenser/filter assembly 2 with filter drive 3, an excitation monochromator 4 with diffraction grating drive 5 (e.g. stepper motor), a reference photo-detector 6, a wavelength calibration photo-detector 7, a cell assembly 8, an absorption photo-detector 9 for absorption spectra measurements, an emission monochromator 10 with diffraction grating drive 11, a wavelength calibration light source 12, and an emission photo-detector 13. A microcontroller unit (controlling means) 14 is provided for device controlling, data processing, and communication with an external computer via different link types. Communicating periodically with grating drives 5 and 11, wavelength calibration photo-detector 7 of the excitation monochromator 4, wavelength calibration light source 12 of the emission monochromator 10, and emission photo-detector 13, the microcontroller 14 performs a task of self-calibration of wavelength scales of both scanning monochromators 4 and 10 providing advanced reliability of the device in fieldwork conditions (transport shocks, vibration, etc). The diffraction grating drives 5 and 11 are preferably stepper motors.

Figure 2:
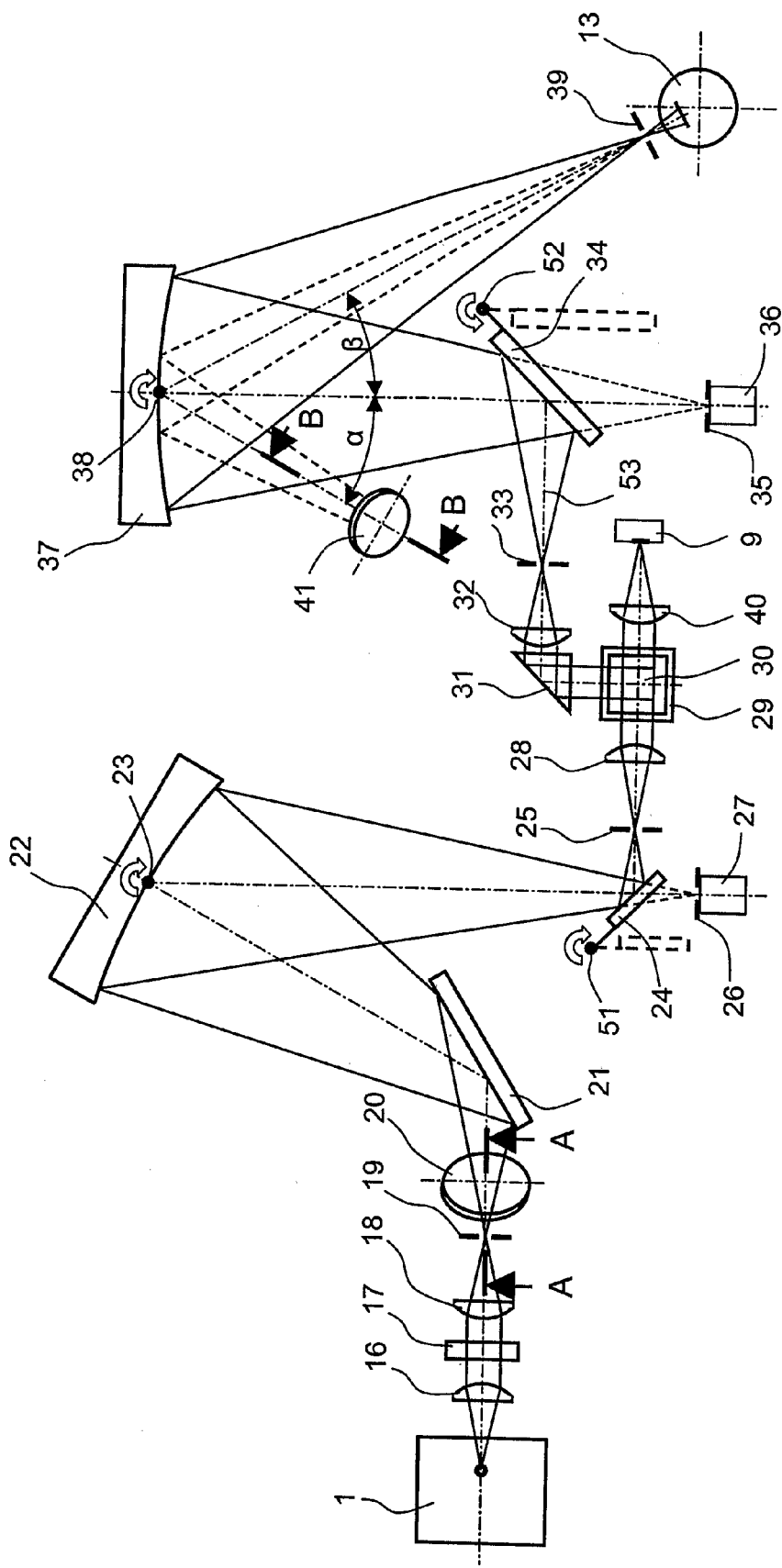
FIG. 2 is a plan schematic view of a first embodiment of the optical layout having a cell for liquid samples.

The plan schematic view of the first embodiment of the optical layout having a cell for liquid samples is shown in FIG. 2. Optical system includes a light source 1, e.g. a Xenon discharge lamp, a collimator lens 16 collecting light from the light source 1 and forming a collimated light beam further focused by a focusing lens 18 onto the entrance slit 19 of the excitation monochromator. As an option a longpass optical filter 17 may be inserted between the collimator lens 16 and focusing lens 18 for cutting off the higher spectral orders present when working in a wide excitation wavelength range from UV to VIS spectrum. Most of the light passed through the entrance slit 19 passes through a plate beamsplitter 20 placed into the diverging light beam at an angle of incidence of 45° and is reflected by a beam inclining plane mirror 21 to a concave diffraction grating 22. The beam-inclining mirror 21 is intended for saving space and makes possible the more compact design of the device.

In the first embodiment the diffraction grating 22 is a holographically recorded aberration corrected concave grating with varied groove spacing and curved grooves, the grating being turnable for wavelength scanning around the vertical axis 23 passing through the grating vertex. The use of an aberration corrected holographic grating leads to a simple and compact mechanical design and provides good spectral image quality on the monochromator exit slit 25 plane over a wide spectral range from UV to VIS. Diffracted and converged by the diffraction grating 22, a light beam of a particular wavelength determined by the grating rotation angle is reflected by a beam inclining mirror 24 towards the monochromator exit slit 25 placed at the locus of the best quality spectrum.

Outgoing through the exit slit 25 a diverging light beam is collimated by a lens 28 and passes through a cell 29 filled with liquid sample 30. Fluorescence light emitted from the sample 30 at an angle of 90° from the excitation beam direction is bent by means of a right angle prism 31 by 90° and focused by a lens 32 onto the entrance slit 33 of the emission monochromator. The diverging light beam passed through the entrance slit 33 is reflected by a beam inclining plane mirror 34 to a concave diffraction grating 37.

In the first embodiment the diffraction grating 37 is a holographically recorded aberration corrected concave grating with varied groove spacing and curved grooves, the grating being turnable for wavelength scanning around the vertical axis 38 passing through the grating vertex. Diffracted and converged by the diffraction grating 37, a light beam of a particular wavelength determined by the grating rotation angle is focused on the plane of the exit slit 39. A photo-detector 13 located behind the slit 39 serves to measure of emission spectra of fluorescence. The photo-detector 13 is preferably a photomultiplier tube.

An absorption photo-detector 9 located behind the cell 29 with liquid sample 30 is used to measure the intensity of excitation light passed through the liquid sample 30 to evaluate it's optical density. A lens 40 serves to focus the collimated excitation light beam onto the absorption photo-detector 9 active area. The absorption photo-detector 9 is preferably a photodiode.

Figure 3:
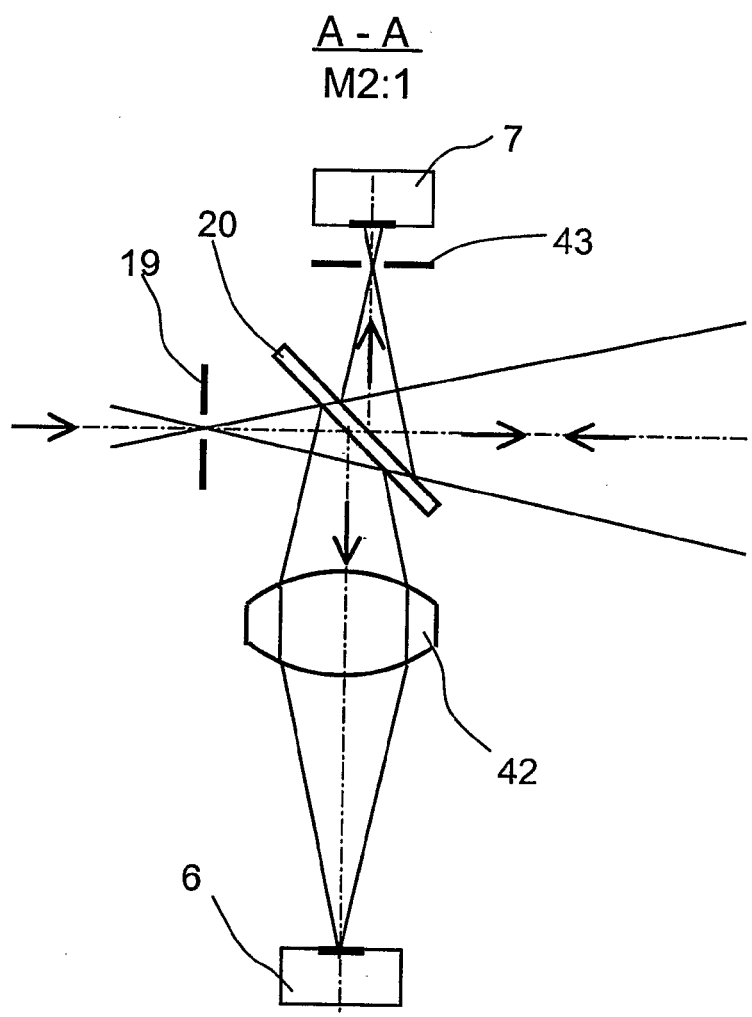
FIG. 3 is a partial sectional view generally taken along the line A-A of FIG. 2.
Figure 4:
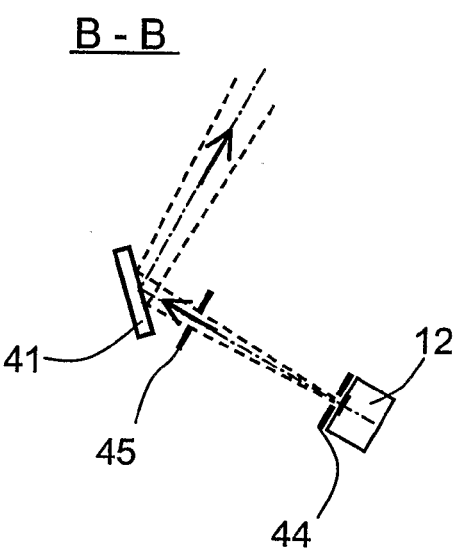
FIG. 4 is partial sectional view generally taken along the line B-B of FIG. 2.

Characteristic feature of the first embodiment of the device lie in the presence of the means for self-calibration of wavelength scales of both monochromators shown in FIGS. 3 and 4. FIG. 3 shows a partial sectional view generally taken along the line A-A of FIG. 2. A wavelength calibration photo-detector 7 (e.g. a photodiode) is located behind the (additional) third exit slit 43 of the excitation monochromator; the third exit slit 43 being located in the locus of the partly reflected from the beamsplitter's 20 facing the grating 22 side and focused by the grating "zero-order" spectrum (i.e. the spectral order which contains all wavelengths of light reflected by the grating). The wavelength calibration photo-detector 7 detects a signal maximum at the grating angular position wherein the grating normal at its vertex coincides with the optical axis of incident light beam on the grating. At this grating angular position light with a known wavelength determined by the grating constant and the beam deviation angle (angle between straight lines connecting the entrance slit and exit slit centers with the grating vertex) is passing through the first or the second exit slit, 25 and 26 respectively. Microcontroller 14 compares periodically and after each switching on the actual wavelength calibration photo-detector 7 signal maximum position with the preadjusted wavelength scale (e.g. an encoder) connected to the grating drive. If a wavelength scale error is detected, the microcontroller 14 recalibrates the scale.

Wavelength self-calibration means of the emission monochromator are illustrated in the FIGS. 2 and 4: a wavelength calibration light source 12 is located at the (additional) third entrance slit 44 of the emission monochromator (see FIG. 4); a diaphragm 45 serves for restricting the beam divergence; a beam inclining mirror 41 bends the light beam into the meridional plane of the diffraction grating 37 and directs the slightly diverging beam to the grating center (see FIG. 2). Angle a between the central incident rays from the calibration light source 12 and from the first or the second entrance slit, 33 and 35 respectively, is equal to the emission monochromator deviation angle $\beta$. Thus at the grating 37 angular position wherein the grating normal at its vertex passes through the entrance slit 35 center the photo-detector 13 detects "zero-order" signal maximum from the wavelength calibration light source 12. The light source 12 is switched on by the microcontroller 14 at the time of checking the wavelength scale calibration. Microcontroller 14 compares periodically and after each switching on the actual signal maximum position with the preadjusted wavelength scale (e.g. an encoder) connected to the grating drive. If a wavelength scale error is detected, the microcontroller 14 recalibrates the scale. Angles $\alpha$ and $\beta$ are set equal in this embodiment only for simplification of preadjustment procedures, principally the angle $\alpha$ may have any other value, different from the value of angle $\beta$.

The wavelength calibration light source 12 is an ordinary light emitting diode (LED); there are no requirements for its spectral characterization as it works in so called "zero-order" spectrum.

A reference photo-detector 6 (see FIG. 3) is used to measure the variations of intensity of light passed through the excitation monochromator entrance slit 19 for a fluorescence spectra data acquisition procedure performed by the microcontroller 14. The diverging light beam from the entrance slit 19 is partly reflected from the beamsplitter's 20 facing the slit 19 side and focused by the lens 42 onto the active area of photo-detector 6. Photo-detector 6 signal amplitude may be also used for diagnostics of light source 1 ageing. As an option the ratio of the amplitudes of signals from the wavelength calibration photo-detector 7 and the reference photo-detector 6 may be used for diagnostics of the state of the diffraction grating 22 which reflectance may decrease due to contamination of its active area in case of working in harsh environmental conditions.

Figure 5:
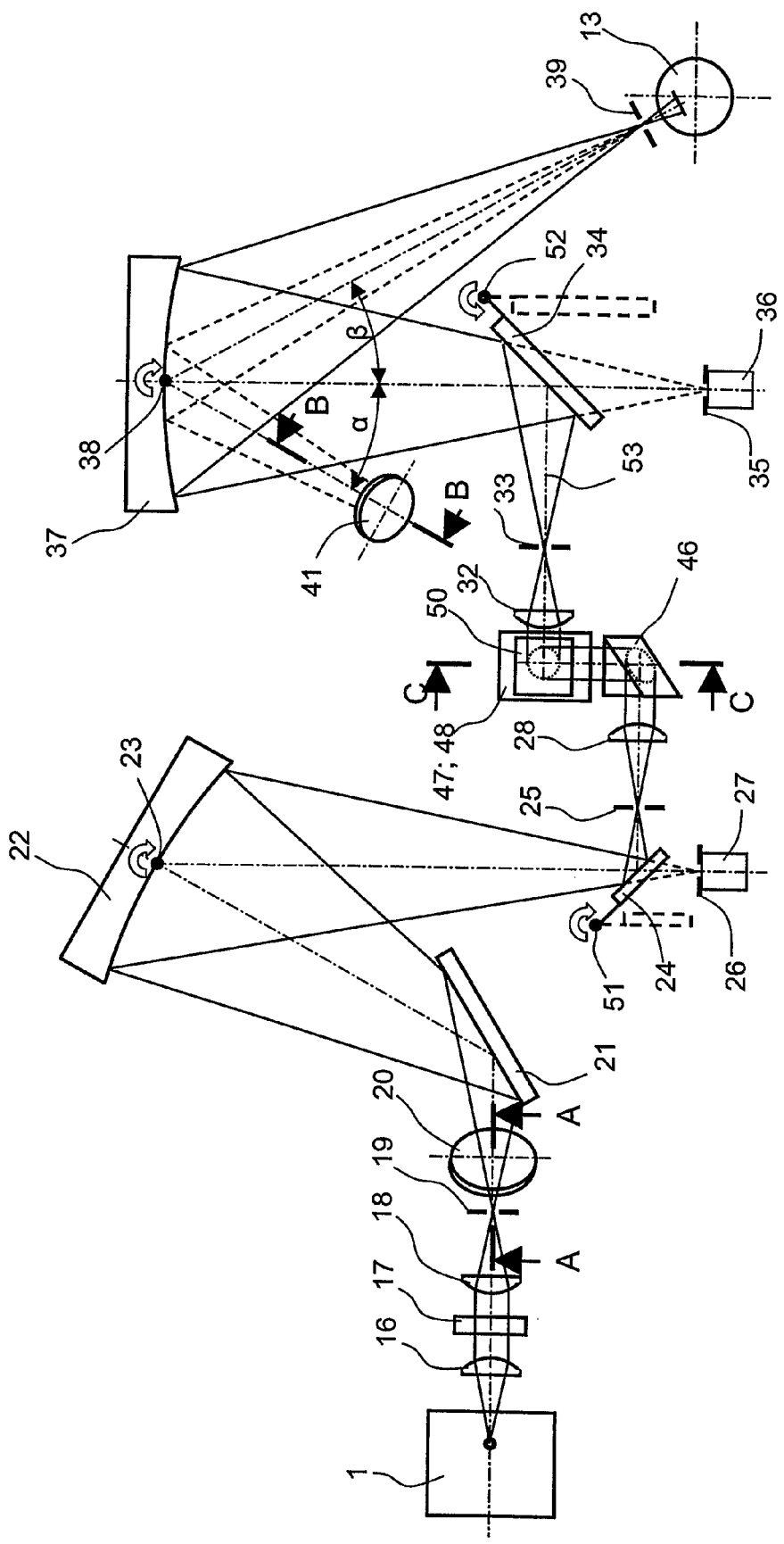
FIG. 5 is a plan schematic view of a second embodiment of the optical layout having a container for dense samples.
Figure 6:
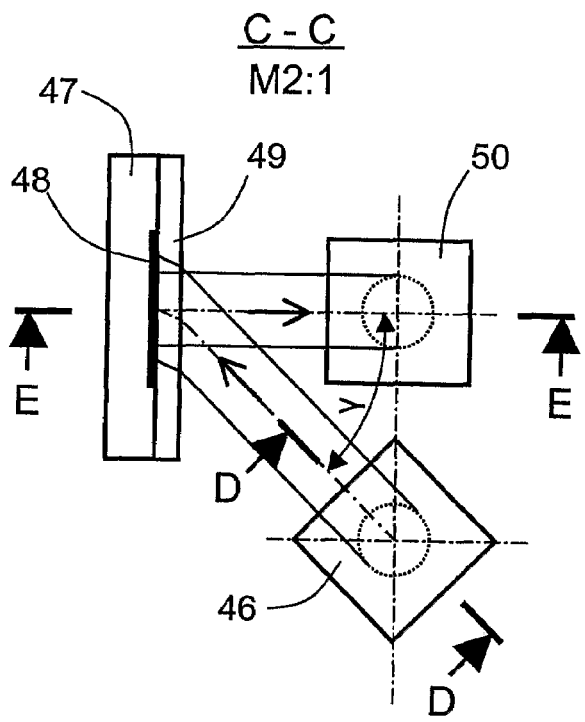
FIG. 6 is a partial sectional view generally taken along the line C-C of FIG. 5.
Figure 7:
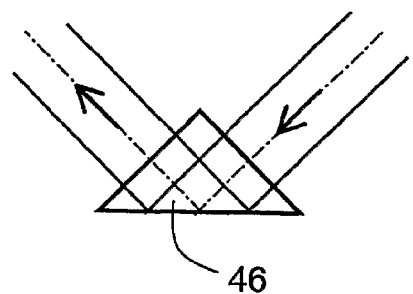
FIG. 7 is a partial sectional view generally taken along the line D-D of FIG. 6.
Figure 8:
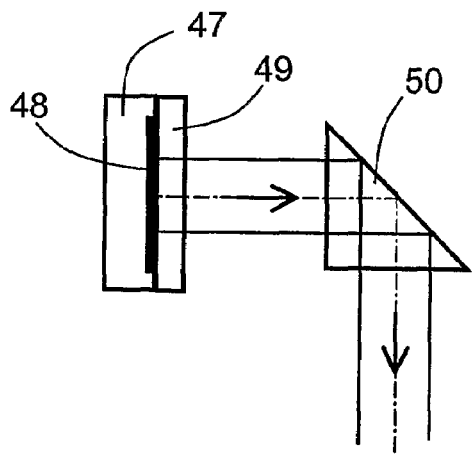
FIG. 8 is a partial sectional view generally taken along the line E-E of FIG. 6.

The second embodiment of the optical layout, which may be located within the first embodiment, having means for measuring dense samples is shown in FIG. 5. This layout is identical to the first preferred embodiment illustrated in FIG. 2 with the exception of changed configuration of the optical cell assembly consisting of a right angle prism 46, a dense sample container 47, a dense sample 48, a transparent cover 49, and a right angle prism 50 (see FIGS. 5-8); also this layout does not contain means for measuring absorption spectra (focusing lens 40 and absorption photo-detector 9 shown in FIG. 2). Outgoing through the exit slit 25 (see FIG. 5), a diverging light beam is collimated by the lens 28 and bent by the right angle prism 46 slantwise downward onto the dense sample 48 located in a cavity of the sample container 47 and covered by the transparent cover 49 (see FIGS. 6-7). By adjusting the angular position of the right angle prism 46 around the optical axis of the light beam incident to the prism the angle of incidence $\gamma$ to the sample cover 49 may be adjusted to a necessary value, generally about 45°. A fluorescence light beam emitted by the sample 48 in the normal direction is bent by means of the right angle prism 50 (see FIG. 8) by 90° and focused by the lens 32 (see FIG. 5) onto the entrance slit 33 of the emission monochromator.

The identity of the basic parts of the first and the second preferred embodiments of the optical layout enables the construction of these two embodiments jointly in the same device having two different interchangeable optical cell assemblies; the first assembly containing the cell 29 for dispose of a liquid sample 30 and the right angle prism 31 (see FIG. 2), the second assembly containing the right angle prism 46, the sample container 47 for dispose of a dense sample 48, the transparent cover 49, and a right angle prism 50 (see FIGS. 5-8). In an alternative construction of the device realizing the both embodiments, the right angle prisms 31 and 50 may be excluded from the respective interchangeable cell assembly and substituted by turnable by 90° around the axis 53 passing through the lens 32 and slit 33 (see FIGS. 2 and 5) centers a single right angle prism added to the main device.

Alternatively and as an option the beam-inclining mirror 24 may be performed as a switching mirror turnable around the axis 51 to remove the mirror from the light path and enable the light beam to exit from the monochromator through an optional second exit slit 26 to an optional optical fiber connector 27 (FIG. 2).

As an option the beam-inclining mirror 34 may be performed as a switching mirror turnable around the axis 52 to remove the mirror from the light path and enable the alternative light beam to enter into the monochromator from an optional optical fiber connector 36 through an optional second entrance slit 35 of the emission monochromator (FIG. 2).

Optical fiber connectors 27 and 36 serve as an option for connection of an alternative external sample measuring device—e.g. a fiber optic immersion fluorescence probe (not described in the present patent application).

The data processing: detection, recognition, quantification, displaying and transfer may be performed by an integrated or an external computer system. A standard pocket PC or any other computer system can be integrated into the device, which would be an internal PC. Alternatively, the processing could be done by a separate unit in a pocket or on the table, which would be an external PC. In the laboratory it is probably more convenient to operate with desktop PC. On site, a pocket PC (integrated or hand-held) is preferable.

In a further embodiment, the method of this invention includes the steps of:

1. Sample preparation: Sampling of a sample and a special sample preparation using tools and kits or automated preparation. If direct measurements are suitable (e.g. for solid or powder samples), this stage may be omitted. Such samples may be introduced into the device by using cell assembly for dense samples.

If a sample requires pre-treatment, the following steps are performed (manually or automatically). The samples for analysis are taken manually by sampling tool (tube or tweezers depending on sample form). A 3 mg of powder or crushed pill that is taken by volumetric tube is dissolved in 150 ml of distilled water in a cup. The water with powder is mixed to complete dilution of the powder in water.

A small amount of dried plant that is taken by tweezers is put into 60 ml of distilled water (or other solvent) in cup and mixed. Then the sample must be filtered The samples can be placed or injected into the active cell of the device manually or automatically accordingly.

Pushing the adequate button (for example, "Cocaine hydrochloride", or "Cocaine base", or "Ecstasy", or "Marijuana", etc.) will be followed by automatic SFS measurements of the sample in the proper measuring conditions.

2. Detection and quantification: Measurements should be done in the specific spectral area to shorten the necessary measurement time and to decrease fluorescence background influence. Measurements have to be done with the appropriate accumulation time and amplification.

Fluorescence measurements of the 3D data (Excitation, Emission, Intensity) may be provided with parallel photometric measurements to control optical density of the liquid sample. (The data related to optical density of the sample are used for proper detection and quantification of the complex substance mixtures).

The data processing: detection, recognition, quantification, displaying and transfer may be performed by an integrated or an external computer system. The expert system detects and quantifies substances of interest automatically. Analysis uses the spectral database with and preliminary compiled calibrated libraries, multivariate calibrations and Neural Nets to solve any kind of the complex detection and quantification problem.

3. Results of measurements: Results should be indicated as text and numbers such as a name of a detected substance of interest and, if it is predetermined, as a concentration number. Concentration may be expressed in weight per volume units or as a percentage from the total sample.

4. Data storage: results have to be automatically stored into the device memory and possibly transferred to a remote different official site as the personal and sample data with the measured raw spectral data, their proper parameters and with the results of detection (quantification) and the date and time of analysis.

An external processing means, such as a PC, a notebook, hand-held etc. is used for database store and final analysis According to different kinds of street drug samples their preparation for measurements may be done using special kit of containers with necessary solvents in predetermined volume or without kit directly into device measuring cell.

Measurements may be done for all forms of samples (powder or solid, or liquid) directly or after automatic preparation. The sample inputted into device may be automatically weighed to calculate measuring data in percents or in concentrations related to the weight of the sample. It may be also automatically diluted according to the device photometric measurements and software algorithm. Each way is predetermined regarding the giving drug or group of drugs analysis.

If the method does not require measurements of liquid form of the sample, the last may be measured outside the device or inside it from the surface of the sample. To provide the method with reliable and simplified liquid sample preparation device may be supplied with sampling tools and special kits: sampling tool for approximate 3 mg of the sample, disposable containers with solvents and a cartridge (holder) to put the container into device for measurements. Preparation of the sample may be done in automatic mode using outer or inner means.

The preparation of the sample can be done in automatic mode using outer means, which is an automatic sampler with dilution, washing and mixing functions. The preparation of the sample can also be done in automatic mode using inner means, which could be a sample preparation panel with dilution, washing and mixing functions.

Personal data of the suspect and a short title for the sample with the date of analysis may be initially entered into device memory using its keyboard.

The device provides SFS detection and quantification of the substances of interest in the range 5-100% of the sample taken for analysis. All data are stored and available as spectra with parameters of their measurements and date.

EXAMPLE 1

Detection of Cocaine in experimental samples: Experimental samples were prepared based upon known common ingredients of Cocaine street samples and their ratio (information from experts and literature): Cocaine hydrochloride; Lidocaine or Caffeine, or Procaine (as adulterants) and Glucose or Lactose, or Baking soda, or Corn Starch (as diluents) with Cocaine presence from 100% to 5%. 3 mg of the following samples dissolved in water, diluted 1:150 and measured for Cocaine detection (see Table 1 below for results):

TABLE 1

Results of Cocaine detection in experimental samples.

| Samples | Composition | Results |
|---|---|---|
| 1 | caf85%_co5% | Yes |
| 2. | caf100% | No |
| 3 | caf100% | No |
| 4 | co85%_caf5%_g10% | Yes |
| 5 | co85%_caf5%_l10% | Yes |
| 6 | co85%_caf5%_s10% | Yes |
| 7 | co85%_lid5%_g10% | Yes |
| 8 | co85%_lid5%_l10% | Yes |
| 9 | co85%_caf5%_g5% | Yes |
| 10 | co85%_caf5%_l10% | Yes |
| 11 | co85%_caf5%_s10% | Yes |
| 12 | co85%_caf5%_st10% | Yes |
| 13 | co85%_lid5%_g10% | Yes |
| 14 | co85%_lid5%_g10% | Yes |
| 15 | co85%_lid5%_l10% | Yes |
| 16 | co85%_lid5%_s10% | Yes |
| 17 | co85%_lid5%_st10% | Yes |
| 18 | co85%_lid3_0204a.dat | Yes |
| 19 | co85%_lid3_0304a.dat | Yes |
| 20 | co85%_prc5%_g10% | Yes |
| 21 | co85%_prc5%_l10% | Yes |
| 22 | co85%_prc5%_s10% | Yes |
| 23 | co85%_prc5%_st10% | Yes |
| 24 | co85%_prc15% | Yes |
| 25 | co85%_prc15% | Yes |
| 26 | co85%_prc5%_g10% | Yes |
| 27 | co85%_prc5%_l10% | Yes |
| 28 | co85%_prc5%_st10% | Yes |
| 29 | co90%_g10% | Yes |
| 30 | co90%_l10% | Yes |
| 31 | co90%_s10% | Yes |
| 32 | co90%_st10% | Yes |
| 33 | co95%_caf5% | Yes |
| 34 | co95%_caf5% | Yes |
| 35 | co95%_lid5% | Yes |
| 36 | co95%_lid5% | Yes |
| 37 | co95%_prc5% | Yes |
| 38 | co95%_prc5% | Yes |
| 39 | co100% | Yes |
| 40 | g100% | No |
| 41 | l5%_co95% | Yes |
| 42 | l100% | No |
| 43 | lid100% | No |
| 44 | prc15%_co85% | Yes |
| 45 | prc20%_co80% | Yes |
| 46 | prc100% | No |
| 47 | prc100% | No |
| 48 | prc100% | No |
| 49 | s100% | No |
| 50 | st95%_co5% | Yes |
| 51 | st100% | No |

Samples Definitions:
co—Cocaine;
caf—Caffeine;
lid—Lidocaine;
prc—Procaine;

TABLE 1-continued

Results of Cocaine detection in experimental samples.

| Samples | Composition | Results |
|---|---|---| g—Glucose;
l—Lactose;
s—Baking Soda;
st—Corn Starch.

Detection and quantification of Cocaine in experimental samples: Experimental samples were prepared based upon known common ingredients of Cocaine street samples and their ratio (information from experts and literature): Cocaine hydrochloride; Lidocaine or Caffeine, or Procaine (as adulterants) and Glucose or Lactose, or Baking soda, or Corn Starch (as diluents). Cocaine presence in the range from 85% up to 100%.

3 mg of the samples were dissolved in water, diluted 1:150 and measured for Cocaine quantification (see Table 2 below for results):

TABLE 2

Results of Cocaine detection and quantification in experimental samples.

| Samples | Composition | Results | Error, % |
|---|---|---|---|
| 1 | caf100% | | |
| 2 | co85%_caf5%_g10% | Cocaine 84.7% | 0.4 |
| 3 | co85%_caf5%_l10% | Cocaine 83.7% | 1.5 |
| 4 | co85%_caf5%_s10% | Cocaine 85.6% | 0.7 |
| 5 | co85%_caf5%_st10% | Cocaine 84.8% | 1.1 |
| 6 | co85%_lid5%_g10% | Cocaine 82.6% | 2.8 |
| 7 | co85%_lid5%_l10% | Cocaine 85.1% | 0.1 |
| 8 | co85%_lid5%_s10% | Cocaine 87.7% | 3.2 |
| 9 | co85%_lid5%_st10% | Cocaine 88.1% | 3.7 |
| 10 | co85%_lid15% | Cocaine 81.3% | 4.3 |
| 11 | co85%_lid15% | Cocaine 81.5% | 4.1 |
| 12 | co85%_prc15% | Cocaine 85.4% | 0.5 |
| 13 | co85%_prc5%_g10% | Cocaine 87.4% | 2.9 |
| 14 | co85%_prc5%_l10% | Cocaine 85.8% | 1.1 |
| 15 | co85%_prc5%_s10% | Cocaine 83.9% | 1.3 |
| 16 | co85%_prc5%_st10% | Cocaine 82.7% | 2.7 |
| 17 | co100% | Cocaine 95.4% | 4.6 |
| 18 | g100% | | |
| 19 | l100% | | |
| 20 | lid100% | | |
| 21 | prc100% | | |
| 22 | prc100% | | |
| 23 | s100% | | |
| 24 | st100% | | |

Samples Definitions:
co—Cocaine;
caf—Caffeine;
lid—Lidocaine;
prc—Procaine;
g—Glucose;
l—Lactose;
s—Baking Soda;
st—Corn Starch.

EXAMPLE 2

Detection of Marijuana in experimental samples: Experimental samples were prepared based upon known common ingredient of street samples of Marijuana (information from experts and literature):
  Marijuana 5% plus tobacco 95%
  Marijuana 30% plus tobacco 70%
  Marijuana 50% plus tobacco 50%
  Marijuana 70% plus tobacco 30%
  Marijuana 100%

Tobacco 100% (as zero point).

Tobacco was taken from Canadian cigarettes: du Maurier Light®; du Maurier Extra Light® and Belmont Milds®, and USA cigarettes: Marlboro®; Camel®; Winstont®; Salem® and Kool®.

3-6 mg of Marijuana were mixed with 3-6 ml of Ethanol, diluted 1:10 and measured for Marijuana detection (see Table 1 below for results of detection).

TABLE 1

Results of Marijuana detection in experimental samples.

| Samples | Composition | Results |
|---|---|---|
| 1 | blmnt100% | No |
| 2 | blmnt100% | No |
| 3 | blmnt100% | No |
| 4 | camel100% | No |
| 5 | kool100% | No |
| 6 | mj5%_camel95% | Yes |
| 7 | mj5%_kool95% | Yes |
| 8 | mj5%_mrlbr95% | Yes |
| 9 | mj5%_salem95% | Yes |
| 10 | mj5%_wnstn95% | Yes |
| 11 | mj10%_salem90% | Yes |
| 12 | mj10%_wnstn90% | Yes |
| 13 | mj15%_mrlbr85% | Yes |
| 14 | mj15%_salem85% | Yes |
| 15 | mj30%_blmnt70% | Yes |
| 16 | mj30%_camel70% | Yes |
| 17 | mj30%_kool70% | Yes |
| 18 | mj30%_mrlbr70% | Yes |
| 19 | mj30%_salem70% | Yes |
| 20 | mj30%_wnstn70% | Yes |
| 21 | mj50%_blmnt50% | Yes |
| 22 | mj50%_blmnt50% | Yes |
| 23 | mj50%_mrel50% | Yes |
| 24 | mj50%_mrl50% | Yes |
| 25 | mj50%_camel50% | Yes |
| 26 | mj50%_kool50% | Yes |
| 27 | mj50%_salem50% | Yes |
| 28 | mj50%_wnstn50% | Yes |
| 29 | mj70%_blmnt30% | Yes |
| 30 | mj70%_camel30% | Yes |
| 31 | mj70%_kool30% | Yes |
| 32 | mj70%_mrlbr30% | Yes |
| 33 | mj70%_salem30% | Yes |
| 34 | mj70%_wnstn30% | Yes |
| 35 | mj100% | Yes |
| 36 | mj100% | Yes |
| 37 | mj100% | Yes |
| 38 | mrel100% | No |
| 39 | mrl100% | No |
| 40 | mrlbr100% | No |
| 41 | salem100% | No |
| 42 | wnstn100% | No |

Samples Definitions:
mj—Marijuana;
blmnt—Belmont Milds ®;
camel—Camel ®;
kool—Kool ®;
mre—du Maurier Light ®;
mrel—du Maurier Extra Light ®;
mrlbr—Marlboro ®;
salem—Salem ®;
wnstn—Winston ®.

The invention claimed is:

1. A portable device for on-site detection and quantification of drugs in a sample comprising:
an ultraviolet-visible light source;
a condenser assembly collecting and focusing light from the light source into a light beam;
an excitation monochromator including an entrance slit, a first diffraction grating turnable around an axis, a first diffraction grating drive, and a first exit slit; the monochromator diffracting and focusing the light beam from the light source on a particular excitation wavelength;
a cell assembly, including a collimator lens, an active cell for receiving a liquid sample of any optical density, a focusing lens, a first right angle reflector, a second right angle reflector, a third right angle reflector and a dense sample container having a transparent window for receiving a dense sample, the assembly collimating the excitation light beam from the excitation monochromator, the sample receiving the excitation light beam and emitting fluorescence beam;
an absorption photo-detector, located behind the cell assembly, receiving the excitation light beam from the cell assembly and measuring the intensity of the excitation light beam passed through the sample evaluating the optical density of the sample, when the sample is a liquid sample;
an emission monochromator including a first entrance slit, a second diffraction grating turnable around an axis, a second diffraction grating drive, and an exit slit; the monochromator diffracting and focusing the fluorescence beam from the cell assembly on a particular emission wavelength;
a wavelength calibration photo-detector, located behind a second exit slit of the excitation monochromator, receiving converging light beam straightly reflected from the diffraction grating, detecting a signal which is maximum at a particular grating angular position;
a wavelength calibration light source, located in front of a second entrance slit of the emission monochromator providing a slightly diverging light beam to the diffraction grating;
an emission photo-detector, located behind the exit slit of the emission monochromator, receiving the fluorescence beam and measuring the emission spectra, the photo-detector also receiving the light beam from the wavelength calibration light source straightly reflected by the diffraction grating at a particular angular position;
a controlling means with a power source and linked to the first and second grating drives, to the wavelength calibration photo-detector, to the wavelength calibration light source, and to the emission photo-detector, the controlling means including an integrated computer system providing operation and pre-analysis control, activating the photo-detector, activating the wavelength calibration light source, receiving the data from the emission and wavelength calibration photo-detectors; comparing after each switching of the device the actual wavelength calibration photo-detector signal maximum position with a preadjusted wavelength scale connected to the first grating drive and the emission photo-detector signal maximum position, the wavelength calibration light source being switched on, with a preadjusted wavelength scale connected to the second grating drive, recalibrating the respective scale if detecting a wavelength scale error;
a memory means, linked to the emission photo-detector, to the absorption photo-detector and to the controlling means for storing the detection and quantification data, and
a data outlet means linked to the controlling means and to the memory means for transferring the detection and quantification data to a remote site.

2. A portable device according to claim 1, wherein the first right angle reflector is a right angle prism.

3. A portable device according to claim 1, wherein the first right angle reflector is a plane mirror.

4. A portable device according to claim 1, wherein the dense sample is a powder.

5. A portable device according to claim 1, wherein the excitation monochromator comprises a plate beamsplitter located in the light path between the entrance slit and the first diffraction grating.

6. A portable device according to claim 5, wherein the excitation monochromator comprises a reference photo-detector for measuring the intensity of light partly reflected from the plate beamsplitter, the signal from the reference photo-detector being transferred to the controlling means and used for normalizing the emission spectra, the reference photo-detector signal amplitude being also used for measuring the intensity of the ultraviolet-visible light source to control its ageing.

7. A portable device according to claim 1, wherein the excitation monochromator comprises a plate beamsplitter located in the light path behind the exit slit.

8. A portable device according to claim 1, wherein the excitation monochromator comprises a first beam inclining plane mirror.

9. A portable device according to claim 1, wherein the excitation monochromator comprises a second beam inclining mirror.

10. A portable device according to claim 1, wherein the emission monochromator comprises a third beam inclining mirror.

11. A method according to claim 10, wherein the calculated concentration ranges from 5% to 100%.

12. A portable device according to claim 1, wherein the condenser assembly comprises a longpass optical filter inserted between a collimator lens and a focusing lens for cutting off any higher spectral orders present in the ultraviolet-visible light source, the filter being controlled by a drive linked to the controlling means.

13. A portable device according to claim 1, wherein the excitation monochromator comprises a first beam inclining mirror located in the light path between the first diffraction grating and the exit slit and the emission monochromator includes a third beam inclining mirror located in the light path between the entrance slit and the second diffraction grating.

14. A portable device according to claim 13, wherein the first beam inclining mirror comprises a switching mirror turnable around an axis to remove the switching mirror from the light path and enable the light beam to exit from the excitation monochromator through a third exit slit to an excitation optical fiber connector, wherein the third beam inclining mirror comprises a second switching mirror turnable around an axis to remove the second switching mirror from the light path and enable the light beam to enter into the emission monochromator from an emission optical fiber connector through a third entrance slit of the emission monochromator.

15. A portable device according to claim 1, adapted to interconnect with an external computer system to perform data processing.

16. A portable device for on-site detection and quantification of drugs in a sample comprising:
an ultraviolet-visible light source;
a condenser assembly collecting and focusing light from the light source into a light beam;
an excitation monochromator including an entrance slit, a first diffraction grating turnable around an axis, a first diffraction grating drive, and a first exit slit; the monochromator diffracting and focusing the light beam from the light source on a particular excitation wavelength;
a cell assembly, including a collimator lens, an active cell for receiving a liquid sample of any optical density, a right angle reflector, and a focusing lens; the assembly collimating the light beam from the excitation monochromator, the sample receiving the excitation beam and emitting fluorescence beam;
an absorption photo-detector, located behind the cell assembly, receiving the excitation beam from the cell assembly and measuring the intensity of the excitation beam passed through the sample evaluating the optical density of the sample;
an emission monochromator including a first entrance slit, a second diffraction grating turnable around an axis, a second diffraction grating drive, and an exit slit; the monochromator diffracting and focusing the fluorescence beam from the cell assembly on a particular emission wavelength;
a wavelength calibration photo-detector, located behind a second exit slit of the excitation monochromator, receiving converging light beam straightly reflected from the first diffraction grating, detecting a signal which is maximum at a particular grating angular position;
a wavelength calibration light source, located in front of a second entrance slit of the emission monochromator providing a slightly diverging light beam to the second diffraction grating;
an emission photo-detector, located behind the exit slit of the emission monochromator, receiving the fluorescence beam and measuring the emission spectra, the photo-detector also receiving the light beam from the wavelength calibration light source straightly reflected by the second diffraction grating at a particular angular position;
a controlling means with a power source and linked to the first and second grating drives, to the wavelength calibration photo-detector, to the wavelength calibration light source, and to the emission photo-detector, the controlling means including an integrated computer system providing operation and pre-analysis control, activating the photo-detector, activating the wavelength calibration light source, receiving the data from the emission and wavelength calibration photo-detectors; comparing after each switching of the device the actual wavelength calibration photo-detector signal maximum position with a preadjusted wavelength scale connected to the first grating drive and the emission photo-detector signal maximum position, the wavelength calibration light source being switched on, with a preadjusted wavelength scale connected to the second grating drive, recalibrating the respective scale if detecting a wavelength scale error;
a memory means, linked to the emission photo-detector, to the absorption photo-detector and to the controlling means for storing the detection and quantification data, and
a data outlet means linked to the controlling means and to the memory means for transferring the detection and quantification data to a remote site.

17. A portable device according to claim 16, wherein the right angle reflector is a right angle prism.

18. A portable device according to claim 16, wherein the right angle reflector is a plane mirror.

19. A portable device for on-site detection and quantification of drugs in a sample comprising:
an ultraviolet-visible light source;
a condenser assembly collecting and focusing light from the light source into a light beam;
an excitation monochromator including an entrance slit, a first diffraction grating turnable around an axis, a first diffraction grating drive, and a first exit slit; the monochromator diffracting and focusing the light beam from the light source on a particular excitation wavelength;

a cell assembly, including a collimator lens, a first right angle reflector, a dense sample container having a transparent window for receiving a dense sample, a second right angle reflector, and a focusing lens; the assembly collimating the light beam from the excitation monochromator, the sample receiving the excitation beam and emitting fluorescence beam;

an emission monochromator including a first entrance slit, a second diffraction grating turnable around an axis, a second diffraction grating drive, and an exit slit; the monochromator diffracting and focusing the fluorescence beam from the cell assembly on a particular emission wavelength;

a wavelength calibration photo-detector, located behind a second exit slit of the excitation monochromator, receiving converging light beam straightly reflected from the first diffraction grating, detecting a signal which is maximum at a particular grating angular position;

a wavelength calibration light source, located in front of a second entrance slit of the emission monochromator providing a slightly diverging light beam to the second diffraction grating;

an emission photo-detector, located behind the exit slit of the emission monochromator, receiving the fluorescence beam and measuring the emission spectra, the photo-detector also receiving the light beam from the wavelength calibration light source straightly reflected by the second diffraction grating at a particular angular position;

a controlling means with a power source and linked to the first and second grating drives, to the wavelength calibration photo-detector, to the wavelength calibration light source, and to the emission photo-detector, the controlling means including an integrated computer system providing operation and pre-analysis control, activating the photo-detector, activating the wavelength calibration light source, receiving the data from the emission and wavelength calibration photo-detectors; comparing after each switching of the device the actual wavelength calibration photo-detector signal maximum position with a preadjusted wavelength scale connected to the first grating drive and the emission photo-detector signal maximum position, the wavelength calibration light source being switched on, with a preadjusted wavelength scale connected to the second grating drive, recalibrating the respective scale if detecting a wavelength scale error;

a memory means, linked to the emission photo-detector and to the controlling means for storing the detection and quantification data, and a data outlet means linked to the controlling means and to the memory means for transferring the detection and quantification data to a remote site.

20. An automated method of analysis of a suspected sample for detection and quantification of illegal drugs in the sample comprising the steps of:

in advance selecting and fixating excitation and emission spectral windows and spectral resolution so as to cover specific fluorescence excitation and emission spectral ranges of predetermined sets of drugs, adulterants and diluents and determining excitation and emission spectral fluorescence patterns of the predetermined sets of drugs in the presence of the predetermined sets of adulterants and diluents;

in advance preparing emission and excitation calibration curves for every spectral fluorescence pattern determined;

obtaining the sample by any means known in the art;

preparing the sample if required, using any suitable sample preparing means;

measuring the spectral fluorescence signature of the prepared sample in the selected and fixed excitation and emission spectral windows with the selected and fixed spectral resolution and recording it as a matrix of fluorescence intensities categorized by excitation and emission wavelength;

red-shifting the emission spectra in the matrix relative to the excitation wavelength to exclude Rayleigh scattering from the measured signature;

normalizing every point of the matrix by the value of a spectral reference channel measured simultaneously with the spectral fluorescence signature;

processing the spectral fluorescence signature by identifying similar spectral patterns in the spectral fluorescence patterns; and applying the calibration curves to derive a proper fluorescence intensity of the sample and calculate its concentration.

21. A method according to claim 20, further comprising the steps of:

in advance selecting and fixating an adsorption spectral window and spectral resolution so as to cover specific absorption excitation and emission spectral ranges of predetermined sets of drugs, adulterants and diluents and determining absorption spectral fluorescence patterns of the predetermined set of drugs in the presence of the predetermined sets of adulterants and diluents;

in advance preparing absorption calibration curves for every absorption spectral fluorescence pattern determined;

measuring the absorption spectral fluorescence signature of the prepared sample in the selected and fixed absorption spectral window with the selected and fixed spectral resolution;

normalizing each of the measured absorption spectral fluorescence signatures by the value of an absorption spectral reference channel measured simultaneously with the absorption spectral fluorescence signature;

processing the absorption spectral fluorescence signatures by identifying similar spectral patterns in the spectral fluorescence patterns; and applying the absorption calibration curves to derive a proper absorption fluorescence intensity of the sample and calculate its concentration.

22. A method according to claim 20, wherein the sample is in solid form.

23. A method according to claim 20, wherein the sample is in powder form.

24. A method according to claim 23, wherein the step of preparing the sample comprises the step of adding a fixed amount of non-fluorescing powder to a fixed amount of the sample.

25. A method according to claim 20, wherein the sample is in viscous form.

26. A method according to claim 20, wherein the sample is in liquid form of a any optical density.

27. A method according to claim 20, wherein the sample is a natural sample.

28. A method according to claim 20, wherein the sample is a chemical sample.

29. A method according to claim 20, wherein the step of preparing the sample comprises the steps of:
- adding a fixed amount of liquid to a fixed amount of the sample;
- exposing the liquid and sample mixture for a predetermined time period to permit optimal extraction or dilution of any illegal drugs; and
- retaining and filtering the liquid portion of the liquid and sample mixture.

30. A method according to claim 29, wherein if the sample is suspected to contain marijuana, the liquid is ethanol.

31. A method according to claim 29, wherein the liquid is distilled water.

32. A method according to claim 20, wherein the result of the analysis comprises:
- the name of the detected substance;
- a quantification of the concentration of the detected substance, and
- the date and time of the analysis.

33. A method according to claim 20, comprising the step of automatically weighing the sample.

* * * * *